United States Patent [19]

Silvestrini

[11] 4,282,237

[45] Aug. 4, 1981

[54] METHOD WITH SUBSTITUTED 1-BENZYL-1H-INDAZOLE-3-CARBOXYLIC ACIDS FOR INTERRUPTING PREGNANCY IN MAMMALS

[75] Inventor: Bruno Silvestrini, Rome, Italy

[73] Assignee: Aziende Chimiche Riunite Angelini Francesco A.C.R.A.F. S.p.A., Rome, Italy

[21] Appl. No.: 932,062

[22] Filed: Aug. 8, 1978

Related U.S. Application Data

[63] Continuation of Ser. No. 741,161, Nov. 11, 1976, abandoned.

[30] Foreign Application Priority Data

Dec. 1, 1975 [IT] Italy ................................ 29845 A/75

[51] Int. Cl.$^2$ ............................................ A61K 31/415
[52] U.S. Cl. ........................ 424/273 N; 424/DIG. 12; 424/DIG. 14

[58] Field of Search ............... 424/273 B, 274, 273 N, 424/DIG. 12, DIG. 14

[56] References Cited

U.S. PATENT DOCUMENTS 3,895,026  7/1975  Palazzo ........................... 424/274 X

OTHER PUBLICATIONS

Lau, Chem. Abs., vol. 80, 1974, Ab. No. 104302t.
Burberi, Exp & Molec Pathol, vol. 23, No. 2, 1975, pp. 308–320.

*Primary Examiner*—Anna P. Fagelson
*Attorney, Agent, or Firm*—Ladas & Parry

[57] ABSTRACT

This invention relates to the use of substituted 1-benzyl-1H-indazole-3-carboxylic acids to interrupt pregnancy. These compounds are described in the U.S. Pat. No. 3,895,026 assigned to the same assignee of the present patent application.

4 Claims, No Drawings

METHOD WITH SUBSTITUTED 1-BENZYL-1H-INDAZOLE-3-CARBOXYLIC ACIDS FOR INTERRUPTING PREGNANCY IN MAMMALS

This is a continuation of application Ser. No. 741,161, filed Nov. 11, 1976, now abandoned.

BACKGROUND OF THE INVENTION

The compounds of the U.S. Pat. No. 3,895,026 belong to a class of substituted 1-benzyl-1Hindazole-3-carboxylic acids, amides and esters having the Formula (I)

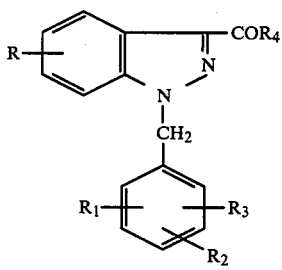

wherein
R is H, $CH_3$, $OCH_3$, halogen;
$R_1$ is H, $CH_3$, halogen or a residue of condensed benzene ring;
$R_2$ is halogen, $CH_3$, $OCH_3$, $CF_3$, $CONH_2$, $SO_2CH_3$;
$R_3$ is H, halogen;
$R_4$ is OH, $NH_2$, $OR_5$;
$R_5$ being a residue easily hydrolyzed in the animal body to yield OH, for instance $-CH_2CH_2OH$, $-CH_2CHOHCH_2OH$, $-CH-(CH_2OH)_2$, and the pharmaceutically acceptable salts of these compounds.

DESCRIPTION OF THE PRIOR ART

The compounds were noted to have antispermatogenic effects. The synthesis of the compound is described in said U.S. Pat. No. 3,895,026.

Some papers describe in detail the antispermatogenic activity and chemical properties of the compounds (Corsi et al., Journal of Medicinal Chemistry 19: 778 (1976); Burberi, S. et al., Exp. and Molec. Pathol. 23: 308-320 (1975); Coulston et al., Exp. and Molec. Pathol. 23: 357-366 (1975); De Martino, C. et al., 23: 321-356 (1975); Silvestrini, B. et al., Exp. and Molec. Pathol. 23: 288-307 (1975). In the above-mentioned patent the antispermatogenic activity was reported as the main property. It was also mentioned that the compounds have a potential use in females to inhibit ovulation and treat sterility by the mechanism of subsequent rebound.

SUMMARY OF THE INVENTION

The new activity claimed in the present application is unrelated to the above-mentioned properties, namely it is unrelated to the antispermatogenic action, inhibition of ovulation and treatment of sterility, exhibited by the compounds of Formula I. Some well studied examples of compounds showing such type of activity in rats are 1-o-chlorobenzyl-1H-indazole-3-carboxylic acid, 1-m-chlorobenzyl-1H-indazole-3-carboxylic acid, 1-p-chlorobenzyl-1H-indazole-3-carboxylic acid, 1-p-fluorobenzyl-1H-indazole-3-carboxylic acid, 1-p-bromobenzyl-1l H-indazole-3-carboxylic acid, 1-(2,4-dichlorobenzyl)-1H-indazole-3-carboxylic acid and their glyceryl esters.

At this purpose it is well known that the so-called female "pill", i.e., the contraceptive presently used, contains two hormones which are fundamental for the maintenance of pregnancy. In other words, the female pill exerts an inhibitory effect on ovulation on the one hand, and a favorable effect on pregnancy on the other.

To the contrary, the compounds used in the present invention have not only the potential inhibitory effect on ovulation (which was mentioned in Applicant's previous U.S. Pat. No. 3,895,026) but also the surprising ability to interrupt pregnancy, instead of protecting it as in the case of the female pill. This abortive effect of these compounds is surprising in view of previous experience and knowledge with other antifertility agents.

It is well known that the mechanism involved in pregnancy are completely different from the mechanisms involved in ovulation. Moreover, my studies have demonstrated that the compounds interrupt pregnancy at doses which are completely devoid of any activity on ovulation. The compounds have the ability to interrupt pregnancy and to cause resorption of the fetus at doses which are far below the toxic ones. On the basis of the available data the compounds may be used in human medicine to interrupt pregnancy. It is well known that such agents are needed under the following circumstances:

(a) to interrupt pregnancy when the mother has been submitted to teratogenic agents;
(b) to interrupt pregnancy when it has occurred against the mother's will;
(c) in family planning as an alternative to already available contraceptives.

The compounds utilized in the process of this invention are utilizable in humans as pills or other pharmaceutically suitable oral dosage forms. The effective dose is comprised between about 100 and 1,000 mg. a day, i.e., from about 2 to 20 mg./kg. p.o. This relatively wide range depends on the different individual sensitivity to treatments of this type and can be readily determined by the physician. The maximum dosage is lower than that perfectly tolerated in laboratory animals even after prolonged treatments.

Moreover, these compounds may be used to interrupt pregnancy in harmful species, such as rats.

EXPERIMENTAL

The attached table indicates the results obtained with 1-(2,4-dichlorobenzyl)-1H-indazole-3-carboxylic acid or clondazolic acid.

TABLE 1

Effects of 1-(2,4-dichlorobenzyl)-1H-indazole-3-carboxylic acid or clondazolic acid on pregnancy in rats. The compound was given daily from day 6–15 of gestation.

| Doses (mg./kg. p.o.) | 0 | 9 | 17 | 35 | 70 |
|---|---|---|---|---|---|
| No. of mothers | 20 | 12 | 10 | 10 | 11 |
| % of resorptions | 13 | 12 | 33 | 74 | 98 |

I claim:
1. A process for interrupting pregnancy and causing resorption of the fetus in a pregnant female which comprises administering to said female an effective amount therefor of at least one compound belonging to the class of substituted 1-benzyl-1H-indazole-3-carboxylic acids, amides and esters having the Formula (I)

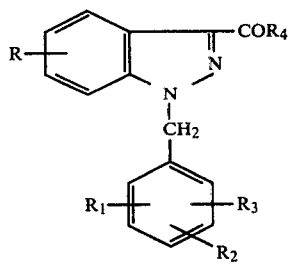

wherein
R is H, CH₃, OCH₃, halogen;
R₁ is H, CH₃, or halogen;

R₂ is halogen, CH₃, OCH₃, CF₃, CONH₂, SO₂CH₃;
R₃ is H, halogen;
R₄ is OH, NH₂, OR₅;
R₅ being an easily hydrolyzable group —CH₂ CH₂ OH, —CH₂ CHOH CH₂OH or —CH(CH₂OH)₂, and the pharmaceutically acceptable salts of these compounds.

2. A process according to claim 1, wherein said effective amount comprises between about 2 to 20 mg./kg. p.o.

3. A process according to claim 1, wherein the compound of formula I is 1-(4-chlorobenzyl)-1H-indazole-3-carboxylic acid.

4. A process according to claim 1, wherein the compound of formula I is 1-(2,4-dichlorobenzyl)-1H-indazole-3-carboxylic acid.

* * * * *